United States Patent
Batcho et al.

[11] Patent Number: 6,040,461
[45] Date of Patent: Mar. 21, 2000

[54] SYNTHESIS OF 3-EPI VITAMIN $D_3$ METABOLITES AND ANALOGS

[75] Inventors: Andrew David Batcho, North Caldwell; Percy Sarwood Manchand, Montclair; Milan Radoje Uskokovic, Upper Montclair, all of N.J.

[73] Assignees: Hoffmann-La Roche Inc., Nutley, N.J.; Syntex (U.S.A.), Palo Alto, Calif.

[21] Appl. No.: 09/310,084

[22] Filed: May 11, 1999

Related U.S. Application Data

[60] Provisional application No. 60/085,521, May 14, 1998.
[51] Int. Cl.⁷ .............................. C07D 303/04; C07F 9/28
[52] U.S. Cl. .................................. 549/332; 568/16; 568/17
[58] Field of Search .............................. 549/332; 568/16, 568/17

[56] References Cited

U.S. PATENT DOCUMENTS

| | | |
|---|---|---|
| 5,145,846 | 9/1992 | Baggiolini et al. . |
| 5,428,029 | 6/1995 | Doran et al. . |
| 5,512,554 | 4/1996 | Baggiolini et al. . |

FOREIGN PATENT DOCUMENTS

| | | |
|---|---|---|
| 808 833 | 11/1997 | European Pat. Off. . |
| WO 98/51663 | 11/1998 | WIPO . |

OTHER PUBLICATIONS

Kiegel, J. et al., Tetr. Lett. 32: pp. 6058–6060 (1991).
Baggiolini, et al., Journal of Organic Chemistry 51, pp. 3098–3108 (1986).
Steinmeyer et al., Steroids, vol. 57(9), pp. 447–452, 1992.

*Primary Examiner*—Johann Richter
*Assistant Examiner*—Taofiq A. Solola
*Attorney, Agent, or Firm*—George W. Johnston; Patricia S. Rocha-Tramaloni; Robert A. Silverman

[57] ABSTRACT

The invention relates to a process for the preparation of vitamin $D_3$ compounds of formula I.

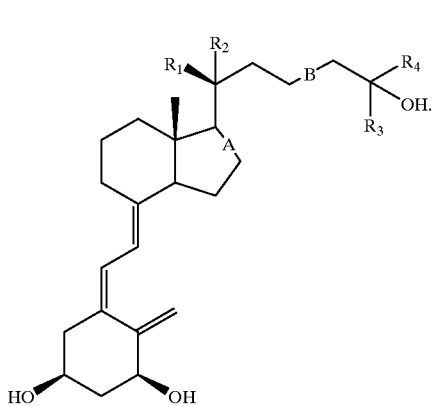

Wherein A is a single or a double bond; B is a single, cis-double, trans double or a triple bond; $R_1$ and $R_2$ are independently hydrogen, a lower alkyl, e.g., a $C_1$–$C_4$ alkyl; $R_3$ and $R_4$ are independently a lower alkyl, e.g., $C_1$–$C_4$ alkyl, a hydroxyalkyl, and a haloalkyl, e.g., a fluoroalkyl; and X and Y are independently hydrogen or hydroxy in the case when B is a single or a double bond.

3 Claims, No Drawings

SYNTHESIS OF 3-EPI VITAMIN $D_3$ METABOLITES AND ANALOGS

This application claims priority under 35 USC § 119(e) of Provisional Application Ser. No. 60/085,521, filed May 14, 1998.

The invention relates to a process for the preparation of vitamin $D_3$ compounds of formula I.

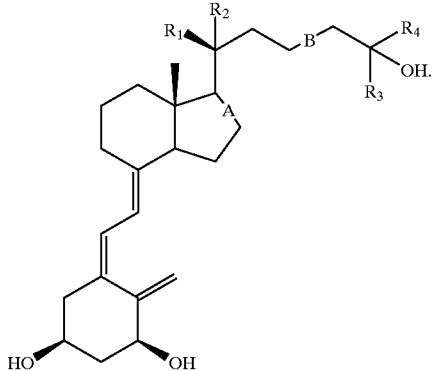

Wherein A is a single or a double bond; B is a single, cis-double, trans double or a triple bond; $R_1$ and $R_2$ are independently hydrogen, a lower alkyl, e.g., a $C_1$–$C_4$ alkyl; $R_3$ and $R_4$ are independently a lower alkyl, e.g., $C_1$–$C_4$ alkyl, a hydroxyalkyl, and a haloalkyl, e.g., a fluoroalkyl; and X and Y are independently hydrogen or hydroxy in the case when B is a single or a double bond.

The compounds of formula I are useful in the preparation of pharmaceutical compositions as is described in WO 98/51663, which corresponds to U.S. patent application Ser. No. 09/080,026, filed May 5, 1998 which claims priority to U.S. Patent Application Ser. No. 60/046,643, filed May 16, 1997.

The 3-epi vitamin $D_3$ analogs of formula I are formed by a convergent synthesis shown in the following Scheme I. Compounds of formula I are prepared by reacting anion corresponding to the compound of formula II, which is preformed by reaction of compound of formula II with n-butyllithium at −78° C. in anhydrous tetrahydrofuran, with compounds of formula III, followed by removal of the protecting silyl groups with tetra-n-butylammonium fluoride in tetrahydrofuran at room temperature.

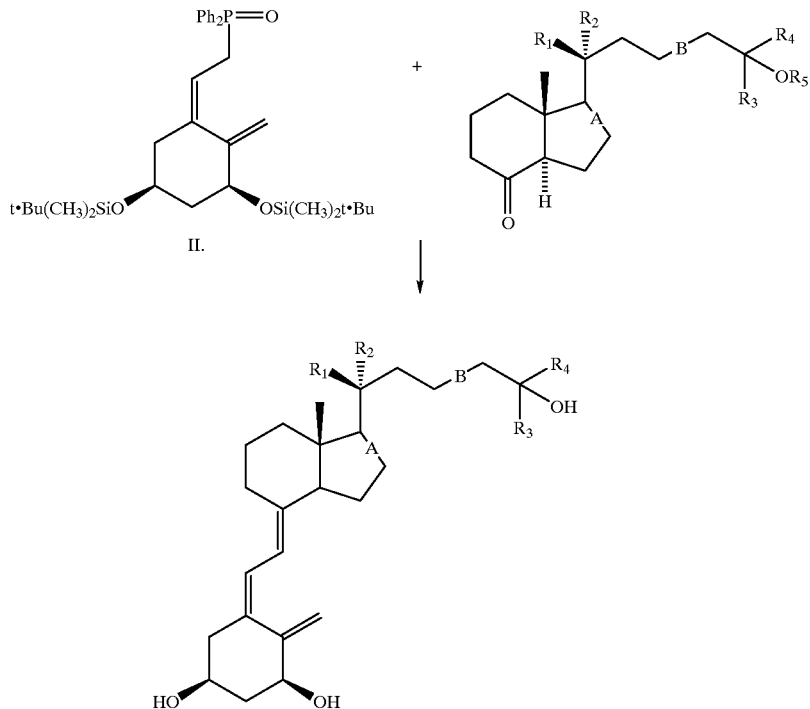

where $R_1$, $R_2$, $R_3$, $R_4$, A and B are as specified above $R_5$ is trimethylsilyl

SCHEME II

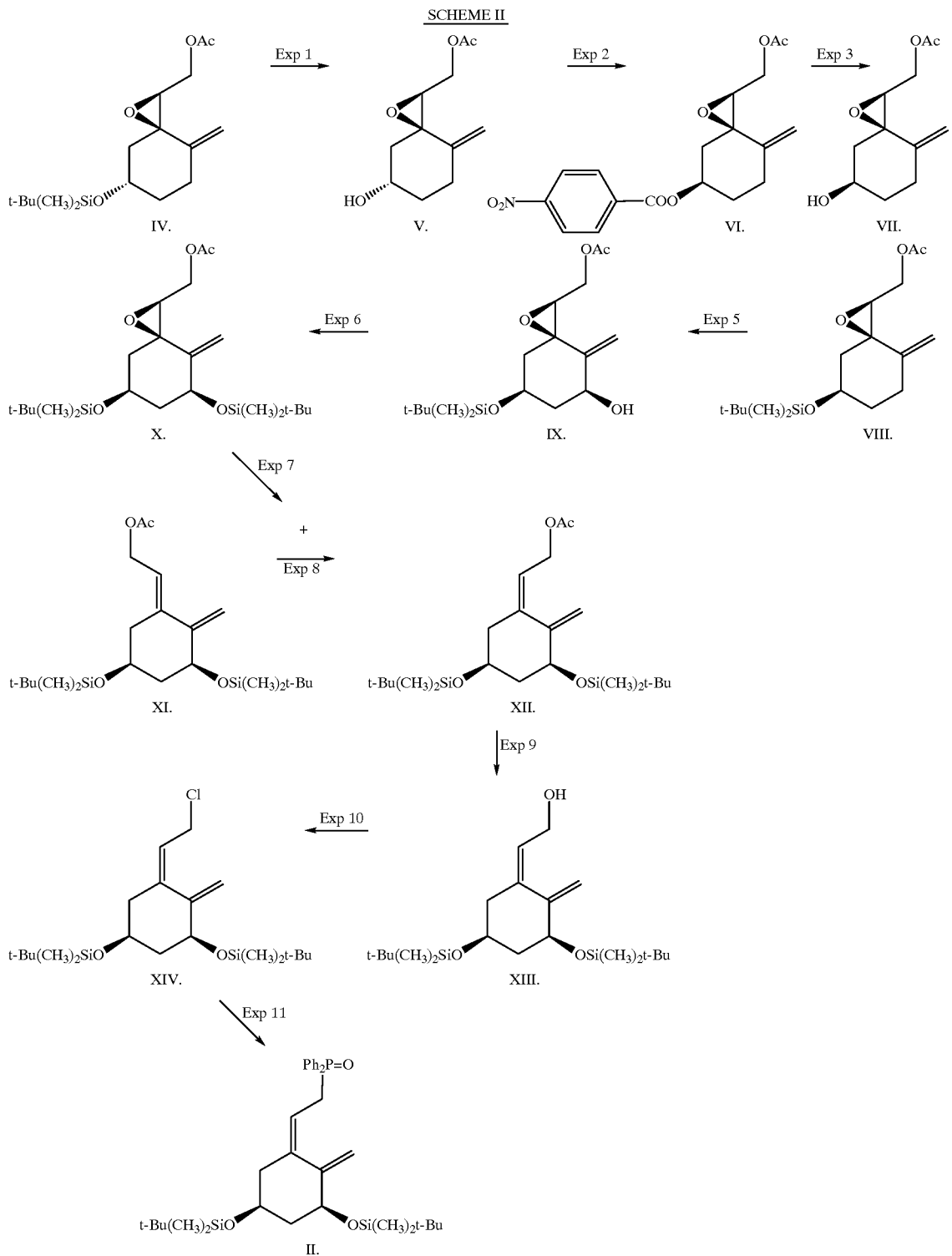

As it is shown in Scheme II, compound of the formula II is prepared by a sequence of reactions starting from the known compound of formula IV. Compound of formula V is obtained by removal of the protecting silyl group with tetra-n-butylammonium fluoride in tetrahydrofuran as a solvent.

Compound of formula VI is obtained by reaction of the compound of formula V with p-nitrobenzoic acid, triphenylphosphine and diethyl azodicarboxylate in toluene as a solvent at 8–10° C. temperature.

Compound of formula VII is obtained by hydrolysis of the compound of formula VI with sodium hydroxide in a mixture of dioxane and water as a solvent.

Compound of formula VIII is obtained from compound of formula VII by reaction with t-butyldimethylsilyl chloride in the presence of imidazole in dimethylformamide as a solvent.

Compound of formula IX is obtained from compound of formula VIII by oxidation with selenium dioxide and tert.-butylhydroperoxide in dioxane as a solvent at the temperature of 88° C.

Compound of formula X is obtained from compound of formula IX by reaction with t-butyldimethylsilyl chloride in the presence of imidazole in dimethyl- formamide as a solvent at room temperature.

Compounds of formula XI and XII as a mixture are obtained from compound of formula X by reaction with anhydrous tungsten hexachloride and n-butyl lithium in the mixture of tetrahydrofuran and hexane as solvent at the temperature below −60° C.

Compound of formula XI in the mixture with compound of formula XII is converted to compound of formula XII by irradiation with a 450-watt Hanovia lamp with uranium core filter in the presence of fluorene in tert.-butyl methyl ether as a solvent at room temperature.

Compound of formula XIII is obtained from compound of formula XII by hydrolysis with sodium hydroxide in ethanol as a solvent.

Compound of formula XIV is obtained from compound of formula XIII by reaction with N-chlorosuccinimide in dichlomethane as a solvent at 0° C. temperature.

Compound of formula II is obtained from compound of formula XIV in a reaction with potassium diphenylphosphide in anhydrous tetrahydrofuran as a solvent at −65° C. temperature, followed by oxidation with 30% hydrogen peroxide in a water-dichloromethane mixture as a solvent at room temperature.

Compounds of formula IIIa to IIIi, shown in Scheme III, are previously known. Compound IIIa was disclosed by Kiegiel J. et al., *Tetrahydron Letters* 32, 6057–6060 (1991). Compound IIIb was disclosed by Baggiolini E. et al., *Journal Organic Chemistry* 51, 3098–3108 (1986). Compounds IIIc, IIIe and IIIf were disclosed in the U.S. Pat. No. 5,145,846. Compound of the formula IIIe was disclosed in the U.S. Pat. No. 5,428,029. Compound of the formula IIIf was disclosed in the U.S. Pat. No. 5,512,554. Compounds IIId and IIIi are described in European Patent Publication No. 808 833.

SCHEME III

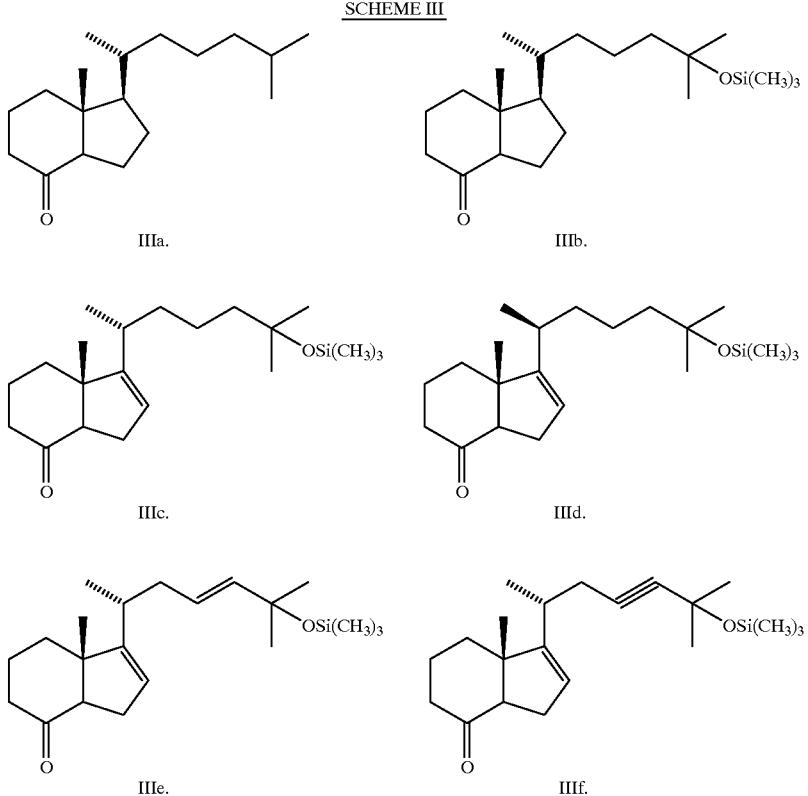

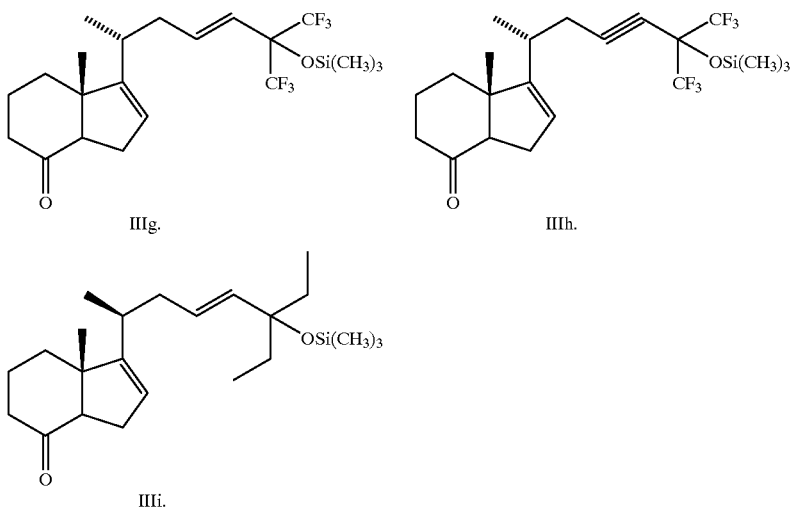

IIIg.   IIIh.

IIIi.

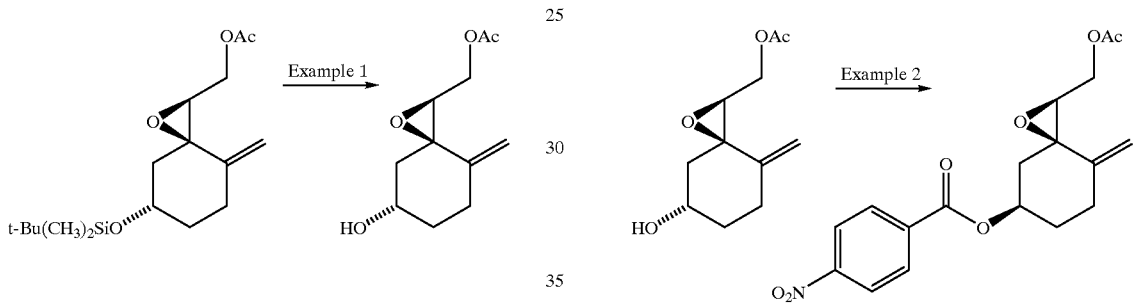

2S-[2α,3α,(R*)]]-7-Hydroxy-4-methylene-1-oxaspiro[2.5]octane-2-methanol acetate

To 220 ml. of 1M tetrabutylammonium fluoride in a 1-L r.b. flask provided with magnetic stirrer and argon atmosphere was added rapidly to 70.5 g. (0.216 mol.) of [2S-[2α,3α,(R*)]]-7-[[(1,1-dimethylethyl)-dimethylsilyl]oxy]-4-meth-ylene-1-oxa-spiro[2.5]octane-2-meth-anol acetate. Complete transfer of the oily silyl ether from its container was effected by rinsing with a total of 150 ml. of tetrahydrofuran. After 22 hr. starting material still remained, so an additional 35 ml. of 1M tetrabutylammonium fluoride was added. After 3 hr. the reaction mixture was poured into 2 L. of water and extracted 4 times with 1 L. of ethyl acetate. The organic phases were washed in a counter-current manner twice with 500 ml. of water. The combined organic phases were evaporated under reduced pressure and the residue chromatographed on 527 g. of silica gel 2) (eluted with 4:1 hexanes-ethyl acetate to ethyl acetate). Recovered starting material 10.94 g. (16%) was followed by 34.46 g. (75% yield) of [2S-[2α,3α,(R*)]]-7-hydroxy-4-methylene-1-oxaspiro[2.5]octane-2-methanol acetate as a colorless oil: [α]S(25,D) +2.7° (c=1.2, CHCl$_3$); MS 213.2 (M+1); $^1$H NMR (CDCl$_3$) δ 2.10 (s, 3H), 2.16 (dd, J=13, 2 Hz, 1H), 2.36 (br d, J=12 Hz, 1H), 2.54 (br t, J=2 Hz, 1H), 3.20 (t, J=5 Hz, 1H), 3.98 (dd, J=12, 6 Hz, 1H), 4.17 (dd, J=12, 5 Hz, 1H), 4.34 (br s, 1H), 4.92 (s, 1H), 4.95 (s, 1H); Anal. Calcd for C$_{11}$H$_{16}$O$_4$: C, 62.25;H, 7.60. Found C, 62.10;H, 7.54.

[2S-[2α,3α,(S*)]]-4-Methylene-7-(4-nitrobenzoyloxy)-1-oxaspiro[2.5]-octane-2-methanol acetate To a suspension of 33.87 g. (203 mmol.) of p-nitrobenzoic acid and 53.24 g. (203 mmol.) of triphenylphosphine in 350 ml. of toluene contained in a 2-L. r. b. flask provided with argon atmosphere and magnetic stirrer was added at 10° (ice/water bath) 35.35 g. (203 mmol.) of diethyl azodicarboxylate rapidly dropwise. The temperature rose to 20°. After five minutes the temperature dropped back to 10° and a solution of 35.84 g. (169 mmol.) of [2S-[2α,3α,(R*)]]-7-hydroxy-4-methylene-1-oxaspiro[2.5]octane-2-metha-nol acetate in 200 ml of toluene was added over about 5 minutes. Precipitation commenced in about 15 minutes. After 3 hours at 8–10° the yellow reaction mixture was poured into 250 ml. of 10% sodium bicarbonate. The suspension was extracted successively with 700 ml. (leaving the undissolved solid with the aqueous phase), 500 ml. (all solids dissolved), and 250 ml. of ethyl acetate. The combined organic phases were dried (Na$_2$SO$_4$), filtered, and evaporated. The residue was triturated with 200 ml. of ether and the insoluble white solid (EtOOC—NH—NH—COOEt and triphenylphospine oxide) was removed by filtration. The filtercake was washed with ether and the white solid checked by nmr and tlc to verify the absence of product. The ether filtrate was evaporated and the residue (89 g.) was chromatographed (medium pressure) on three 0.5 m.×55 mm. columns in series (silica gel G-60) using 4:1 hexanes-ethyl acetate as elution solvent. Twenty-four 250 ml. fractions were collected. Fractions 14–18 (33.64 g.) were pure product. The overlapping fractions (1–13 and 19–24) amounted to 15.41 g and were rechromatographed in the same solvent system using only two 0.5 m.×55 mm. columns in series connected to an automatic fraction collector. A total of 200 25-ml. fractions was eluted. Fractions 61–81 contained 3.62 g. (9% yield) of colorless oil (The nmr was compatible with the corresponding $\Delta^{2,3}$ elimination product.). Fractions 121–170 contained 9.47 g. of product. The combined total from both chromatograms amounted to 43.11 g. (71% yield) of [2S-[2α,3α,(S*)]]-4-methylene-7-(4-nitrobenzoyloxy)-1-oxaspiro[2.5]-octane-2-methanol acetate as an off-white solid. An analytical sample, obtained by recrystallization from ethyl acetate/hexanes, had m.p. 81–82°; [α]S(25,D) −43.4° (c0.98, EtOH); HRMS (M+H), observed 362.1248, theor. 362.1241; $^1$H NMR (CDCl$_3$) δ 1.70 (m, 1H), 1.92 (br d, J=12 Hz, 1H), 2.11 (s, 3H), 2.25 (m, 3H), 2.60 (d, J=13 Hz, 1H), 3.25 (t, J=6 Hz, 1H), 4.02 (dd, J=12, 6 Hz, 1H), 4.10 (dd, J=12, 5 Hz, 1H), 5.03 (s, 1H), 5.05 (s, 1H), 5.26 (m, 1H), 8.20 (d, J=9 Hz, 2H), 8.30 (d, J=9 Hz, 2H); Anal. Calcd for C$_{18}$H$_{19}$NO$_7$: C, 59.83;H, 5.30; N, 3.88. Found: C, 59.27;H, 5.22; N, 3.82.

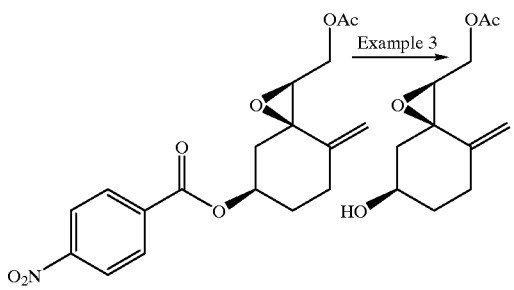

[2S-[2α,3α,(S*)]]-7-Hydroxy-4-methylene-1-oxaspiro[2.5]octane-2-methanol acetate To a vigorously stirred solution of 44.16 g. (122mmol.) of [2S-[2α,3α,(S*)]]-4-methylene-7-(4-nitrobenzoyloxy)-1-oxaspiro[2.51-octane-2-methanol acetate in 500 ml. of dioxane and 50 ml. of water contained in a 3-L 3-necked r.b. flask fitted with thermometer and argon inlet and immersed in an ice-water bath was added at 8° dropwise over 40 min. a solution of 4.88 g (122 mmol.) of sodium hydroxide in 50 ml. of water. After 1 hr. an additional 0.49 g (12 mmol.) of sodium hydroxide pellets was added. Stirring at 8° was continued for an other hour, and then the reaction solution was poured into a 2-L separatory funnel; 100 ml. of brine and 25 ml. of 1N sodium bicarbonate were added followed by extraction 4 times with 1 -L portions of ethyl acetate (the diol is water soluble). The organic phases were dried (Na$_2$SO$_4$), filtered, and the solvents removed on a rotary evaporator. The extracts amounted to 1) 35.28 g. 2) 1.49 g. 3) 0.52 g. 4) 0.14 g. The combined extracts were flash chroma-tographed on 155 g. of silica gel G60 in 4:1 hexanes-ethyl acetate. Elution with 2:1 hexanes-ethyl acetate gave a mixture of di- and mono-esters. Ethyl acetate eluted 5.24 g. (25% yield) of crystalline diol, [2S-[2α,3α,(S*)]]-7-hydroxy-4-methylene-1-oxaspiro[2.5]octane-2-methanol, An analytical sample was recrystallized from acetonitrile to give a white solid, m.p. 90.5–91.5; [α]S(25,D) −2.3° (c0.99, CHCl$_3$); MS (M+H) 171.1; $^1$H NMR (CDCl$_3$) δ 1.42 (m, 1H), 1.74 (dd, J=12, 2 Hz, 1H), 2.01 (m, 3H), 2.45 (m, 1H), 3.12 (m, 3H), 3.54 (s, 2H), 3.91 (br t, 1H), 4.90 (s, 1H), 4.92 (s, 1H); Anal. Calcd for C$_9$H$_{14}$O$_3$: C, 63.51;H, 8.29; N, 3.88. Found: C, 63.66;H, 8.42.

The above ester mixture was chromatographed on two 0.5 m.×55 mm. columns (silica gel G-60) in series (medium pressure) connected to an automatic fraction collector. A total of 283 25-ml. fractions were collected. The earlier fractions consisted of mostly starting material 11.93 g (27% yield) and minor amounts of di p-nitrobenzoate (1.67 g., 3% yield), primary p-nitrobenzoate 3-OH (0.71 g., 2% yield), 3-p-nitrobenzoate primary OH (3.61 g., 9% yield). Fractions 255–282 contained 8.03 g. (31%) of the desired product, [2S-[2α,3α,(S*)]]-7-hydroxy-4-methylene-1-oxaspiro[2.5]octane-2-methanol acetate. as an oil: [α]S(25,D) −7.9° (c1.18, CHCl$_3$); MS (M$^+$), 212.1; $^1$H NMR (CDCl$_3$) δ 1.45 (br dd, 1H), 1.66 (s, 1H), 1.74 (m, 1H), 2.04 (m, 3H), 2.09 (s, 3H), 2.50 (m, 1H), 3.16 (t, J=5 Hz, 1H), 3.95 (m, 2H), 4.10 (dd, J=12, 5 Hz, 1H), 4.97 (s, 2H), 5.26 (m, 1H); Anal. Calcd for C$_{11}$H$_{16}$O$_4$: C, 62.25;H, 7.60. Found: C, 61.50;H, 7.62.

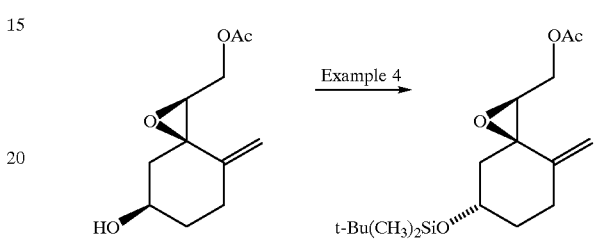

[2α,3α,(S*)]]-7-[[(1,1-dimethylethyl)-dimethylsilyl]oxyl-4-methylene-1-oxaspiro[2.5]octane-2-methanol acetate To a magnetically stirred solution of 20.22 g. (95.2 mmol.) of [2S-[2α,3α,(S*)]]-7-hydroxy-4-methylene-1-oxaspiro[2.5]octane-2-meth-anol acetate and 10.2 g. (150 mmol.) of imidazole in 50 ml. of dimethyl-formamide under an argon atmosphere was added 20.0 g. (133 mmol.) of t-butyldimethylsilyl chloride. The reaction was allowed to stir overnight (14 hr.) and 10 ml. of methanol was added. After 1 hr. the reaction solution was poured into a separatory funnel containing 500 ml. of water. Extraction with 2×250 ml. of hexanes followed by countercurrent backwashes with 2×250 ml. of water, afforded after drying (Na$_2$SO$_4$), filtration, and evaporation under reduced pressure, 32.30 g. of an oil. Chromatography on two 0.5 m.×55 mm. columns (silica gel G-60) in series (medium pressure) using 95:5 hexanes-ethyl acetate gave 29.19 g. (94% yield) of [2α,3α,(S*)]]-7-[[(1,1-dimethylethyl)-dimethylsilyl]oxy]-4-methylene-1-oxaspiro[2.5]octane-2-methanol acetate as a colorless oil: [α]S(25,D) −7.9° (c1.02 CHCl$_3$); MS 326.1; $^1$H NMR (CDCl$_3$) δ 0.066 (s, 3H), 0.072 (s, 3H), 0.88 (s, 9H), 1.42 (br m, 1H), 1.59 (br d, 1H), 1.97 (m, 3H), 2.09 (s, 3H), 2.45 (m, 1H), 3.12 (t, J=5 Hz, 1H), 3.88 (m, 2H), 4.12 (dd, J=12, 5 Hz, 1H), 4.92 (s, 1H), 4.94 (s, 1H); Anal. Calcd for C$_{17}$H$_{30}$O$_4$Si: C, 62.54;H, 9.26; Si, 8.60. Found C, 62.69;H, 9.32; Si, 8.32.

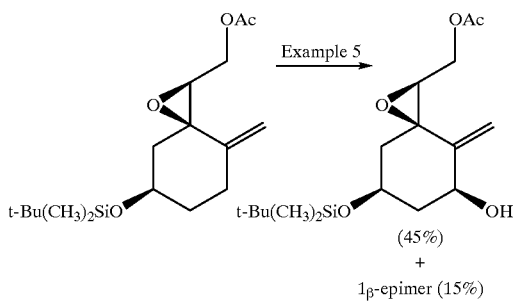

[2α,3α,(R*,S*)]]-7-[[(1,1-dimethylethyl)-dimethylsilyl]oxy]-5-hydroxy-4-methylene-1-oxaspiro[2.5]octane-2-methanol acetate To a 2-L flask provided with mechanical stirrer, argon atmosphere, and thermometer containing a solution of 29.10 g. (89.1 mmol.) of [2α,3α,(S*)]]-7-[[(1,1-dimethylethyl)-dimethylsilyl]oxy]-4-methylene-1-oxaspiro [2.5]octane-2-methanol acetate in 1 L. of dioxane was added 11.1 g. (100 mmol.) of pulverized selenium dioxide followed by 40 ml. of 3 M (120 mmol.) tert.-butylhydroperoxide in 2,2,4-trimethylpentane . The stirred suspension was heated on the steam bath (88° pot temperature) for 7 hr. (the color gradually changed to dirty red), and then allowed to cool overnight. The reaction suspension was poured into a separatory funnel containing a solution of 69 g. (0.5 mol.) of potassium carbonate and 25.2 g. (0.2 mol.) of sodium sulfite in 300 ml. of water. Extraction with 3 L of 2:1 hexanes-ethyl acetate and 1 L of 1:1 hexanes-ethyl acetate followed by successive countercurrent washes with 500 ml. of water, 200 ml. of 1 N sodium carbonate (red color), and 200 ml. of brine gave, after drying the combined organic phases (Na$_2$SO$_4$), filtration and evaporation under reduced pressure, 32.68 g. of reddish oil. Successive flash chromatography on 90 g. and then 200 g. of silica gel G60 using hexanes to 9:1 hexanes-ethyl acetate separated the starting material 2.91 g. (10%) and 3:1 hexanes-ethyl acetate gave the hydroxylated products 21.57 g. Chromatography on three 0.5 m.×55 mm. columns in series (medium pressure) using 20:1 hexanes-isopropanol gave 4.74 g. (14% yield) of minor isomer, [2α,3α,(S*,S*)]]-7-[[(1,1-dimethylethyl)-dimethylsilyl] oxy]-5-hydroxy-4-methylene-1-oxaspiro[2.5]octane-2-methanol acetate as an oil: [α]S(25,D) −54.9° (c1.06, EtOH); MS 342 (M$^+$); $^1$H NMR (CDCl$_3$) δ 0.07 (s, 3H), 0.08 (s, 3H), 0.88 (s, 9H), 1.99 (t, J=12 Hz, 1H), 2.09 (s, 3H), 2.23 (br d, J=14 Hz, 1H), 3.20 (t, J=6 Hz, 1H), 3.90 (dd, J=12, 6 Hz, 1H), 4.24 (dd, J=12, 5 Hz, 1H), 4.33 (m, 1H), 4.52 (br t, 1H), 5.08 (s, 1H), 5.16 (s, 1H); Anal. Calcd for C$_{17}$H$_{30}$O$_5$Si: C, 59.62;H, 8.83; Si, 8.20. Found C, 59.30;H, 8.68; Si, 7.97. and 13.50 g. (45% yield) of major isomer, [2α,3α,(R*,S*)]]-7-[[(1,1-dimethylethyl)-dimethylsilyl] oxy]-5-hydroxy-4-methylene-1-oxaspiro[2.5]octane-2-methanol acetate, as a white solid, which, on recrystallization from hexanes, had m.p. 65–66°: [α]S(25,D) −2.5° (c1.02, EtOH); MS 341 (M−1); $^1$H NMR (CDCl$_3$) δ 0.07 (s, 3H), 0.08 (s, 3H), 0.88 (s, 9H), 1.50 (q, J=l Hz, 1H), 1.60 (br d, J=12 Hz, 1H), 2.02 (t, J=12 Hz, 1H), 2.09 (s, 3H), 3.11 (t, J=5 Hz, 1H), 3.93 (m, 2H), 4.09 (m, 2H), 5.12 (s, 1H), 5.28 (s, 3H); Anal. Calcd for C$_{17}$H$_{30}$O$_5$Si: C, 59.62;H, 8.83; Si, 8.20. Found C, 59.68;H, 8.83; Si, 8.18.

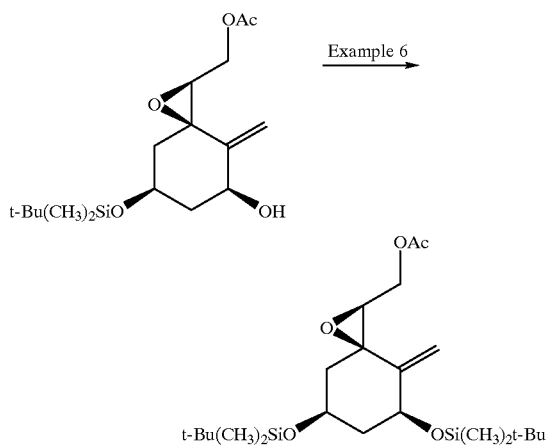

[2α,3α,(R*,S*)]]-5,7-bis-[[(1,1-dimethylethyl)-dimethylsilyl]oxy]-4-methylene-1-oxaspiro[2.5]octane-2-methanol acetate To a magnetically stirred solution of 14.40 g. (42.0 mmol.) of [2α,3α,(R*,S*)]]-7-[[(1,1-dimethylethyl)-dimethylsilyl]oxy]-5-hydroxy-4-methylene-1-oxaspiro[2.5] octane-2-methanol acetate and 5.1 g. (75 mmol.) of imidazole in 60 ml. of dimethylformamide under an argon atmosphere was added 7.54 g. (50 mmol.) of t-butyldimethylsilyl chloride. The reaction was allowed to stir over the weekend (3 days) and then 5 ml. of water was added. After 30 min. the reaction solution was poured into a separatory funnel containing 400 ml. of water. Extraction with 2×400 ml. of 95:5 hexanes-ethyl acetate which were backwashed in a countercurrent manner with 2×300 ml. of water and then combined, dried (Na$_2$SO$_4$), filtered and evaporated under reduced pressure gave 19.13 g. of amberish oil. Chromatography on a 0.5 m.×55 mm. column (silica gel G-60) in (medium pressure) using 10:1 hexanes-ethyl acetate gave 17.57 g. (92% yield) of [2α,3α,(R*,S*)]]-5,7-bis-[[(1,1-dimethylethyl)-dimethylsilyl]-oxy]-4-methylene-1-oxaspiro [2.5]octane-2-methanol acetate as a colorless oil: [α]S(25,D) −4.5° (c1.07, EtOH); MS 457 (M+1); $^1$H NMR (CDCl$_3$) δ 0.06 (s, 12H), 0.88 (s, 9H), 0.92 (s, 9H), 2.01 (t, J=12 Hz, 1H), 2.09 (s, 3H), 3.09 (t, J=6 Hz, 1H), 3.85 (m, 1H), 4.00 (m, 3H), 5.06 (s, 1H), 5.29 (s, 1H); Anal. Calcd for C$_{23}$H$_{44}$O$_5$Si$_2$: C, 60.48;H, 9.71; Si, 12.38, Found C, 60.49;H, 9.68; Si, 12.25.

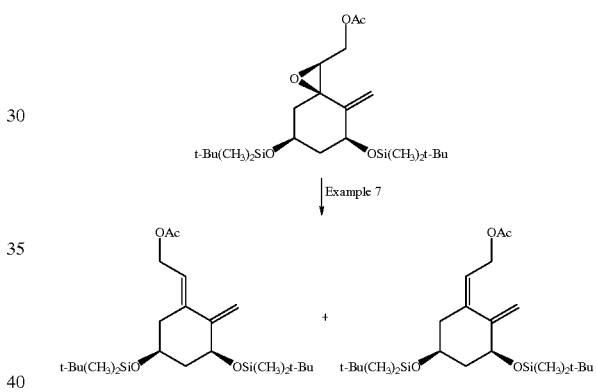

[3R-(3β,5β)]-2-[3,5-Bis[[(1,1-dimethylethyl)-dimethylsilyl]oxy]-2-methylene-cyclohexylidene]-ethanol acetate (cis/trans mixture)

A 3-L. 3-neck flask fitted with argon inlet, mechanical stirrer, and thermometer was charged with 330 ml. of tetrahydofuran and cooled to −70° in a dry ice-acetone bath. Portionwise addition of 46.23 g. (116 mmol.) of anhydrous tunsten hexachloride was carried out while maintaining the temperature below −60° , and then rapid dropwise addition of 225 ml. of 1.6M (360 mmol.) butyllithium in hexanes keeping the temperature below −45° (ca 5 min.). After 5 min. the dry ice-acetone bath was replaced with a ice-water bath. The exotherm caused the temperature to reach 12° before dropping to 5°. Color changes from blue to khaki to reddish black occurred. After 30 min. at 5°, a solution of 17.3 g. (37.9 mmol.) of [2α,3α,(R*,S*)]]-5,7-bis-[[(1,1-dimethylethyl)-dimethyl-silyl]oxy]-4-methylene-1-oxaspiro [2.5]octane-2-methanol acetate in 50 ml. of tetrahydrofuran was added rapidly dropwise over 3 min. After 4.5 hr. the reaction mixture was diluted with 750 ml. of hexanes and rapidly filtered through 400 g. of tlc grade silica gel 60G packed (dry) tightly under vacuum in a 2-L. sintered glass funnel. The filter cake was washed with 2×1 L. of 20:1 hexanes-ethyl acetate. The combined filtrates were evaporated under reduced pressure at 25° bath temperature to give 17.47 g. of oil. Flash chromatography on 157 g. of silica gel G60 gave 16.93 g. of oil. Chromatography on three 0.5 m.×55 mm. columns in series (medium pressure) and elution with 100:1 dichlormethane-ethyl acetate afforded 14.20 g. (85% yield) of [3R-(3β,5β)]-2-[3,5-Bis[[(1,1-dimethylethyl)-dimethylsilyl]oxy]-2-methylene-cyclohexylidene]-ethanol acetate as a 62/38 mixture of trans/cis isomers.

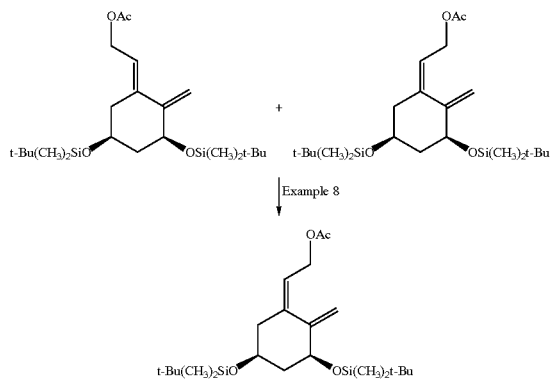

[3R-(1Z,3α,5α)]-2-[3,5-Bis [[(1,1-dimethylethyl)-dimethylsilyl]oxy]-2-methylenecyclohexylidene]-ethanol acetate A solution of 14.13 g. of 3R-(3α,5α)]-2-[3,5-Bis[[(1,1-dimethylethyl)-dimethylsilyl]oxy]-2-methylenecyclohexylidene]-ethanol acetate (62/38 mixture of trans/cis isomers) and 15 g. of fluorene in 500 mol. of tert.-butyl methyl ether was irradiated with a 450-watt Hanovia lamp with uranium core filter for 80 hr. After evaporation of the solvent under reduced pressure, the residue was chromatographed on three 0.5 m.×55 mm. columns in series (medium pressure) in 4 passes (overlapping fractions rechromatographed) using 100:1 dichlormethanethyl acetate to realize 12.88 g. (91% yield) of pure cis isomer [3R-(1Z,3α,5α)]-2-[3,5-Bis[[(1,1-dimethylethyl)-dimethylsilyl]oxy]-2-methylenecyclohexylidene]-ethanol acetate as a colorless oil: $^1$H NMR (CDCl$_3$) δ 0.06 (m, 12H), 0.88 (s, 9H), 0.92 (s, 9H), 2.06 (s, 3H), 3.70 (m, 1H), 3.95 (m, 1H), 4.53 (m, 1H), 4.69 (m, 1H), 4.80 (s, 1H), 5.34 (s, 1H), 5.46 (m, 1H).

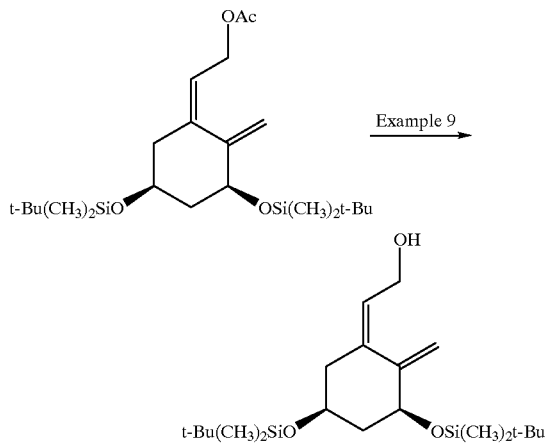

[3R-(1Z,3α,5α)]-2-[3,5-Bis[[(1,1-dimethylethyl)-dimethylsilyl]oxy]-2-methylenecyclohexylidene]-ethanol To a magnetically stirred solution of 12.88 g. (29.22 mmol.) of [3R-(1Z,3α,5α)]-2-[3,5-Bis[[(1,1-dimethylethyl)-dimethylsilyl]oxy]-2-methylenecyclohexylidene]-ethanol acetate in 100 ml. of 2B ethanol under an argon atmosphere was added 2.0 g. (50 mmol.) of sodium hydroxide pellets. After 40 min. the reaction solution was poured into a separatory funnel containing 400 ml. of brine. Extraction with 400 ml. of 5:3 hexanes-ethyl acetate followed by 250 ml. of ethyl acetate with a countercurrent backwash with 200 ml. of brine gave after combining the organic phases, drying (Na$_2$SO$_4$), filtration, and evaporation under reduced pressure gave 11.51 g. of an oil. Chromatography on two 0.5 m.×55 mm. columns in series (medium pressure) using 8:1 hexanes-ethyl acetate gave 10.77 g. (92% yield) of [3R-(1Z,3α,5α)]-2-[3,5-Bis[[(1,1-dimethylethyl)-dimethylsilyl]oxy]-2-methylenecyclohexylidene]-ethanol as a colorless oil: $^1$H NMR (CDCl$_3$) δ 0.07 (s, 6H), 0.08 (s, 3H), 0.09 (s, 3H), 0.88 (s, 9H), 0.93 (s, 9H), 1.56 (m, 2H), 2.17 (m, 2H), 2.43 (m, 1H), 3.73 (m, 1H), 3.96 (m, 1H), 4.14 (m, 1H), 4.29 (dd, J=12, 8 Hz, 11H), 4.77 (s, 1H), 5.33 (s, 1H), 5.55 (m, 11H)

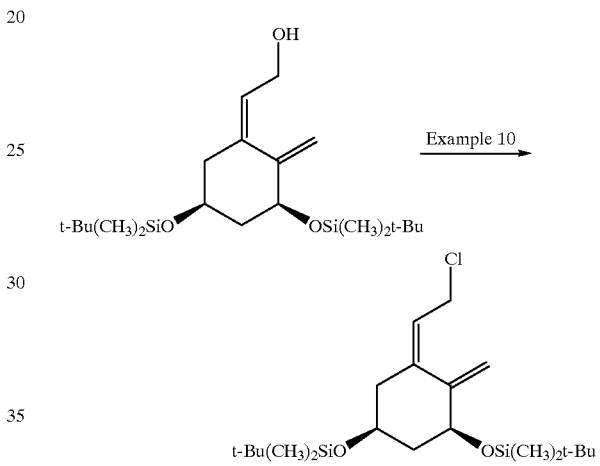

[1S-(1α,3α,5Z)]-[[5-(2-chloroethylidene)-4-methylene-1,3-cylohexanediyl]bis(oxy)]bis[(1,1-dimethylethyl)dimethyl]silane To a stirred solution of 7.80 g. (58.4 mmol.) of N-chlorosuccinimide in 210 ml. of dichloromethane under an argon atmosphere cooled to 2° in an ice-acetone bath was added dropwise over 2 min. 4.5 ml. (61 mmol.) of dimethylsulfide. A white precipitate formed. After 30 min. at 0°, the bath was replaced with dry ice -acetone and the pot temperature adjusted to −20° by partial immersion of the reaction flask. A solution of 10.62 g. (26.6 mmol.) of [3R-(1Z,3α,5α)]-2-[3,5-Bis[[(1,1-dimethylethyl)-dimethylsilyl]-oxy]-2-methylenecyclohexylidene]-ethanol in 30 ml. of dichloromethane was added dropwise over 10 min. After 30 min. the bath was replaced by ice-water and stirring was continued for 2 hr. at 0° to 5° at which time the reaction mixture was transfered to a separatory funnel containing 200 ml. of water. Extraction 2×300 ml. with hexanes followed by backwashes with 2×250 ml. of water in a countercurrent manner afforded, after combining the organic phases, drying (Na$_2$SO$_4$), fil-tration, and evaporation under reduced pressure, 11.3 g. Flash chromatography on 62 g. of silica gel G60 followed by chromatography on a 0.5 m.×55 mm. column (medium pressure) using 95:5 hexanes-ethyl acetate gave 10.53 g. (95% yield) of [1S-(1α, 3α,5Z)]-[[5-(2-chloro-ethylidene)-4-methylene-1,3-cylohexanediyl]bis(oxy)]bis[(1,1-dimethyl-ethyl)dimethyl] silane as a colorless oil: $^1$H NMR (CDCl$_3$) δ 0.06 (m, 12H), 0.88 (s, 9H), 0.93 (s, 9H), 2.15 (m, 1H), 2.42 (m, 1H), 3.70

(m, 1H), 3.92 (m, 1H), 4.12 (m, 2H), 4.95 (s, 1H), 5.37 (s, 1H), 5.55 (m, 1H).

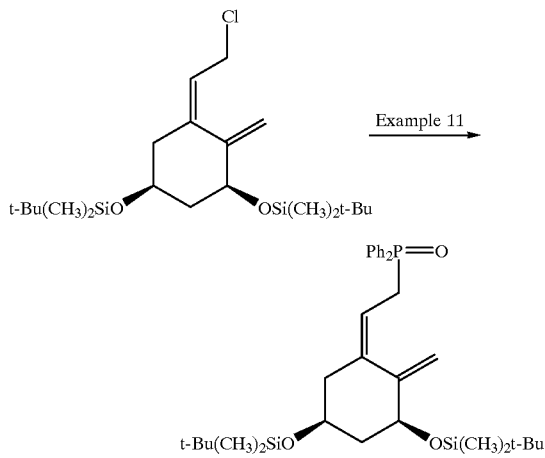

[3S-(1Z,3α,5α)]-2-[3,5-Bis[[(1,1-dimethylethyl)-dimethylsilyl]oxy]-2-methylenecyclohexylidene]ethyl]diphenylphosphine oxide A 1-L. 3-neck flask fitted with argon inlet, thermometer, and mechanical stirrer was charged with a solution of 10.05 g. (24.1 mmol.) of [1S-(1α,3α,5Z)]-[[5-(2-chloroethylidene)-4-methylene-1,3-cylohexanediyl]bis(oxy)]bis[(1,1-dimethylethyl)dimethyl]silane in 125 ml. of freshly distilled anhydrous tetra-hydrofuran and cooled in a dry ice-acetone bath to −65°. Addition of 0.5 M potassium diphenyphosphide in tetrahydrofuran during 30 min. until a red color persisted required 47 ml. After stirring for 1 hr. at −65° 10 ml. of water was added, and the cooling bath removed. The reaction decolorized. Then 200 ml. of dichloromethane was added rapidly followed by 60 ml. of a solution containing 6.6 ml. of 30% hydrogen peroxide. After 1.4 hr 6.6 g. of sodium sulfite followed by 100 ml of brine and 200 ml. of dichloromethane was added. The phases were separated and the aqueous phase was washed with 200 ml of dichloromethane. The organic phases were backwashed in a countercurrent manner with 200 ml of brine. The combined organic phases were dried ($Na_2SO_4$), filtered, and evaporated under reduced pressure to give 16.08 g. of oil, which on medium pressure chromatography a 0.5 m×55 mm column (silica gel G-60), gave 12.22 g. (87% yield) of [3S-(1Z,3α,5α)]-2-[3,5-bis[[(1,1-dimethylethyl)-dimethylsilyl]oxy]-2-methylenecyclohexyli -dene]ethyl] diphenylphosphine oxide as a white solid. An analtyical sample, recrystallized from acetonitrile, had m.p. 97–99°; [α]S(25,D) +5.8°; MS 583(M+1); $^1$H NMR ($CDCl_3$) δ 0.03 (s, 9H), 0.04 (s, 3H), 0.86 (s, 9H), 0.91 (s, 9H), 1.44 (q, J=1 1 Hz, 1H), 2.05 (br m, 2H), 2.37 (br d, 1H), 3.15 (br m, 1H), 3.35 (m, 2H), 3.52 (m, 1H), 4.75 (s, 1H), 5.27 (s, 1H), 5.48 (m, 1H), 7.5 (m, 6H), 7.7 (m, 4H); Anal. Calcd for $C_{33}H_{51}O_3PSi_2$: C, 68.00;H, 8.82; P, 5.31; Si, 9.64. Found C, 67.46;H, 8.74; P, 5.38; Si, 9.63.

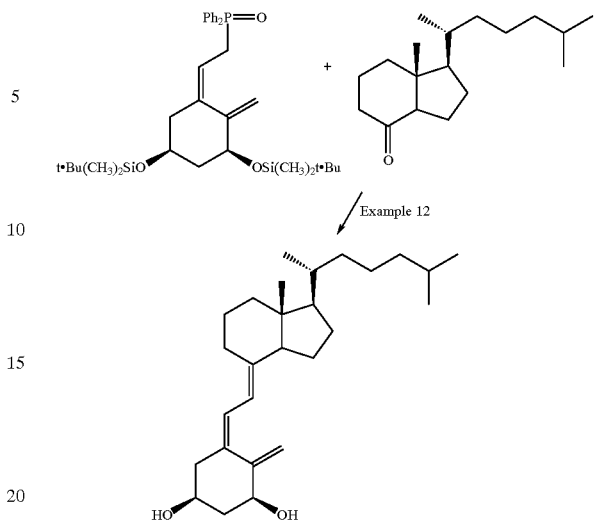

3-epi-1α-Hydroxycholecalciferol. To a stirred, cold (−78° C.) solution of 620 mg (1.06 mmol) of the reagent [3 S-1Z,3α,5α)]-2-[3,5-bis[[(1,1 -dimethylethyl)-dimethylsilyl]oxy]-2-methylenecyclohexylidene]ethyl]diphenylphosphine oxide (Ro 27-5110) in 6.0 mL of anhydrous THF was added 0.66 mL (1.06 mmol) of a 1.6 M solution of n-butyllithium in hexanes. The resultant deep red solution was stirred at −78° C. for 20 mins and treated with 264.4 mg (1.0 mmol) of [1R-1α(R*), 3aα, 7aβ]]-1-[1,5-dimethylhexyl]-octa-hydro-7a-methyl-4H-inden-4-one in 3.0 mL of anhydrous THF. The mixture was stirred at −78° C. for 3.0 hours, allowed to warm to room temperature, and was quenched with 10 mL of a 1:1 mixture of 1.0 M Rochelle salt solution and 1.0 N $KHCO_3$ solution. After 15 minutes, the mixture was poured into a mixture of 60 mL of ethyl acetate and 40 mL of a 1:1 mixture of 1.0 M Rochelle salt solution and 1.0 N $KHCO_3$ solution. The organic phase was separated and the aqueous phase was re-extracted with 3×60 mL of ethyl acetate. The combined organic extracts were washed with 100 mL of 50% brine, dried ($Na_2SO_4$), and evaporated to give 802 mg of a gum, which was purified by flash chromatography on 45 g of silica gel (40–65 μm mesh; 3.5 cm diameter column) with 5% ethyl acetate in hexanes, taking 15-mL fractions. Fractions 5–8 were combined and evaporated to give 561 mg of a colorless gum. The latter was dissolved in 6.0 mL of anhydrous THF and treated with 8.0 mL (8.0 mmol) of a 1.0 M solution of tetra-n-butylammonium fluoride in THF. The mixture was stirred at room temperature for 18 hours, diluted with 15 mL of water, stirred for an additional 15 minutes, and poured into a mixture of 70 mL of ethyl acetate and 50 mL of 10% brine. The organic phase was separated and the aqueous phase was re-extracted with 3×60 mL of ethyl acetate. The combined organic extracts were washed with 4×100 mL of water, dried ($Na_2SO_4$) and evaporated to give 421 mg of a gum, which was purified by flash chromatography with ethyl acetate as eluent, taking 15-mL fractions. Fractions 12–21 were combined and evaporated to give 360 mg of a gum, which was purified by HPLC (10–30 μm mesh silica gel; 70 mL/min; 90% ethyl acetate in hexanes; $R_T$=24 minutes) to give, after evaporation of the solvents, 322 mg of a gum. Crystallization from 10 mL of anhydrous methyl formate at −1° C. for 2 hours afforded 257 mg of the title compound as colorless crystals, mp 115–117° C.; [α]S(25,D) −43.87° (MeOH, c=0.62); UV (MeOH) λmax 263 (ε=18,721), 219 (ε=13,119, shoulder), 214 (ε=14,075) nm; IR (CHCl$_3$) 3607, 3505 cm$^{-1}$; $^1$H NMR (CDCl$_3$) δ 0.54 (3H, s), 0.85 (6H, d, J=5Hz), 0.91 (3H, d, J=6.8Hz), 1.0–2.10(21H, m), 2.42(1H, dd, J=13, 6, Hz), 2.57 (1H, d, J=12 Hz), 2.84 (1H, d, J=12.8 Hz), 4.05 (1H, br s), 4.31 (1H, brt), 5.00 (1H, s), 5.30 (1H, s), 6.01 (1H, d, J=11 Hz), 6.44 (1H, d, J=Hz); MS (EI) m/z 400.4 (M$^+$, 14)

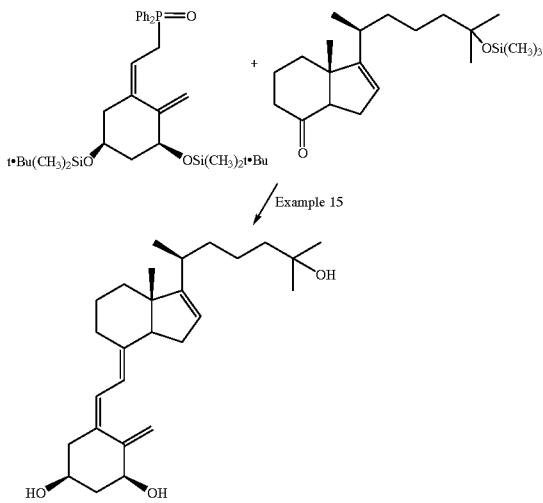

3-epi-1,25-Dihydroxy-16-ene-20-epicholecalciferol. To a stirred, cold (−78° C.) solution of 582.9 mg (1.0 mmol) of the reagent [3S-(1Z,3α,5α)]-2-[3,5-bis[[1,1-dimethyl)-dimethylsilyl]oxy]-2-methylenecyclohexyl-idene]ethyl]ethyl]diphenylphosphine oxide (Ro 27-5110) in 5.0 mL of anhydrous THF was added 0.63 mL (1.0 mmol) of a 1.6 M solution of n-butyllithium in hexanes and the resultant deep red solution was stirred at −78° C. for 15 mins. A solution of 175 mg (0.5 mmol) of [3aR-[1(S*), 3aα,7aβ]]-1-[1,5-dimethyl-5-[(trimethyl-silyl)oxy]hexyl]-3,3a,5,6,7,7a-hexahydro-7a-methyl-4H-inden-4-one in 2.5 mL of anhydrous THF was added and the mixture was stirred at −78° C. for 2.5 hours and at room temperature for 30 minutes. It was quenched with 10 mL of a 1:1 mixture of 2.0 M Rochelle salt solution and 2.0 N KHCO$_3$ solution. After 15 minutes the mixture was poured into 60 mL of ethyl acetate and 40 mL of a 1:1 mixture of 2.0 M Rochelle salt solution and 2.0 N KHCO$_3$ solution. The organic phase was separated and the aqueous phase was reextracted with 3×60 mL of ethyl acetate. The combined organic extracts were washed with 100 mL of 10% brine, dried (Na$_2$SO$_4$) and evaporated to give 702 mg of a gum, which was purified by flash chromatography on silica gel (40–65 μm mesh; 3.5 cm diameter column) with 7.5% ethyl acetate in hexanes as eluent, taking 15-mL fractions. Fractions 4–7 were combined and evaporated to give 310 mg of a colorless gum. The latter was dissolved in 4.0 mL of THF, treated with 4.0 mL (4.0 mmol) of a 1.0 M solution of tetra-n-butylammonium fluoride in THF, and the mixture was stirred at room temperature for 17 hours. The mixture was diluted with 15 mL of water, stirred for 30 minutes and poured into a mixture of 70 mL of ethyl acetate and 50 mL of 10% brine. The organic phase was separated and the aqueous phase was re-extracted with 3×60 mL of ethyl acetate. The combined organic extracts were washed with 4×100 mL of water, dried (Na$_2$SO$_4$) and evaporated to give 214 mg of a gum, which was purified by flash chromatography on 45 g of silica gel (40–65 μm mesh; 3.5 cm diameter column) with ethyl acetate as eluent, taking 15-mL fractions. Fractions 13–26 were combined and evaporated, and the residue was dissolved in 10 mL of methyl formate. The solution was filtered through a 0.4 μm filter and the filtrate was evaporated to give 169 mg of the title compound as a colorless foam: [α]S(25,D) −11.34° (MeOH, c=0.67); UV (MeOH) λmax 264 (c=17310), 218 (ε=13,161, shoulder), 210 (ε=15,961) nm; IR (CHCl$_3$) 3608 cm$^{-1}$; $^1$H NMR 67 0.70 (3H, s), 1.05 (3H, d, J=6.8 Hz), 1.21 (6H, s), 1.22–1.50 (13H, m), 1.57–1.74 (4H, m), 1.97–2.23 (6H, m), 2.35 (1H, m), 2.45 (1H, m), 2.55 (1H, m), 2.64 (1H, d, J=6.8 Hz), 2.83(1H, d, J=12 Hz), 4.04 (1H, br s), 4.31(1H, br s), 5.02 (1H, s), 5.31(2H, s), 6.11 (1H, d, J=11 Hz), 6.43 (1H, d, J=11 Hz); MS (FAB) m/z 414 (M$^+$, 12).

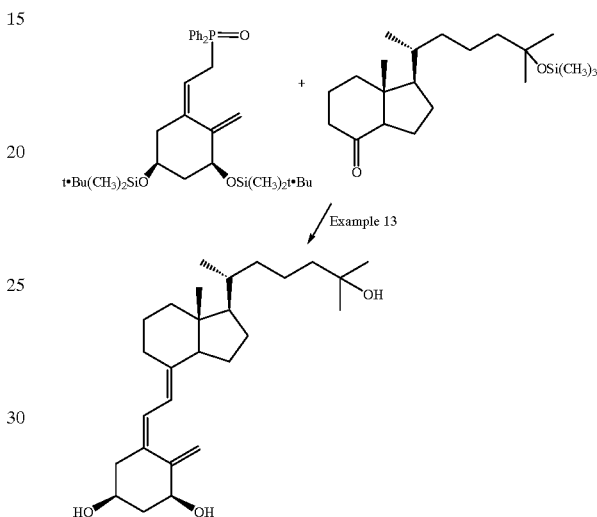

3-epi-1,25-Dihydroxycholecalciferol. To a stirred, cold (−78° C.) solution of 582.9 mg (1.0 mL) of the reagent [3S-(1Z,3α,5α)]-2-[3,5-bis[[(1,1-dimethyl)-dimethylsilyl]oxy]-2-methylenecyclohexylidene]ethyl]diphenylphosphine oxide (Ro 27-5110) in 5.0 mL of anhydrous THF was added 0.63 mL (1.0 mmol) of a 1.6 M solution of n-butyllithium in hexanes. The resultant deep red solution was stirred at −78° C. for 15 minutes and treated with 176 mg (0.5 mmol) of [1R-[1α(R*), 3aα, 7aβ]]-1-[1,5-dimethyl-5-[(trimethylsilyl)oxy]-hexyl]-octahydro-7a-methyl-4H-inden-4-one in 3.0 mL of THF. The mixture was stirred at −78° C. for 2.5 hours, allowed to warm to room temperature, stirred for an additional 30 minutes and quenched with 10 mL of a 1:1 mixture of 2.0 M Rochelle salt solution and 2.0 N KHCO$_3$ solution. After 15 minutes, the mixture was poured into 75 mL of ethyl acetate and 50 mL of a 1:1 mixture of 2.0 M Rochelle salt solution and 2.0 N KHCO$_3$ solution. The organic phase was separated and the aqueous phase was re-extracted with 3×60 mL of ethyl acetate. The combined organic extracts were dried (Na$_2$SO$_4$) and evaporated to give a semisolid, which was purified by flash chromatography on 50 grams of silica gel (40–65 μm mesh; 3.5 cm diameter column) with 8% ethyl acetate in hexanes taking 15-mL fractions. Fractions 4 and 5 were combined and evaporated to give 321 mg of a colorless gum. The latter was dissolved in 5.0 mL of THF and treated with 4.0 mL (4.0 mmol) of a 1.0 M solution of tetra-n-butylammonium fluoride in THF. The mixture was stirred at room temperature for 17.0 hours, diluted with 10 mL of water and, after 15 minutes, poured into a mixture of 75 mL of ethyl acetate and 60 mL of 10% brine. The organic phase was separated and the aqueous phase was re-extracted with 3×70 mL of ethyl acetate. The combined organic extracts were washed with 4×100 mL of water, dried (MgSO$_4$) and evaporated to give 197 mg of a gum, which was purified by flash chromatography on 45 grams of silica gel (40–65 µm mesh; 3.5 cm diameter column) with ethyl acetate as eluent taking 15-mL fractions. Fractions 12–21 were combined and evaporated to give 174 mg of a semisolid, which was dissolved in 15 mL of ethyl acetate. The solution was filtered through a 0.4 µm filter and the filtrate was evaporated to give a solid. Crystallization from 7.0 mL of anhydrous methyl formate at -1° C. overnight to give 160 mg of the title compound as colorless crystals, mp 135–136° C.; [α]S(25,D) -43.88° (MeOH, c=0.72); UV (MeOH) 263 (ε=17,170), 218 (ε=12,405 shoulder), 213 (ε=13191) nm; IR (CHCl$_3$) 3607, 3519 cm$^{-1}$; $^1$H NMR (CDCl$_3$) δ 0.54 (3H, s), 0.93 (3H, d, J=6.8 Hz), 1.05 (1H, m), 1.21 (6H, s), 1.22–1.60 (19H, m), 1.70 (2H, m), 1.90 (1H, m), 1.96–2.09 (4H, m), 2.17 (1H, d, J=5 HzOH), 2.43 (1H, m), 2.56 (1H, d, J=12 Hz), 2.85 (1H, d, J=12.8 Hz), 4.08 (1H, br s) 4.30 (1H, br s), 5.00 (1H, s), 5.30 (1H, s), 6.03 (1H, d, J=12 Hz), 6.43 (1H, d, J=12 Hz); MS (EI) Calcd. for C$_{27}$H$_{44}$O$_3$: m/z 416.3290. Found: m/z 416.3286. The stereo-structure of the title compound was confirmed by a single crystal X-ray analysis.

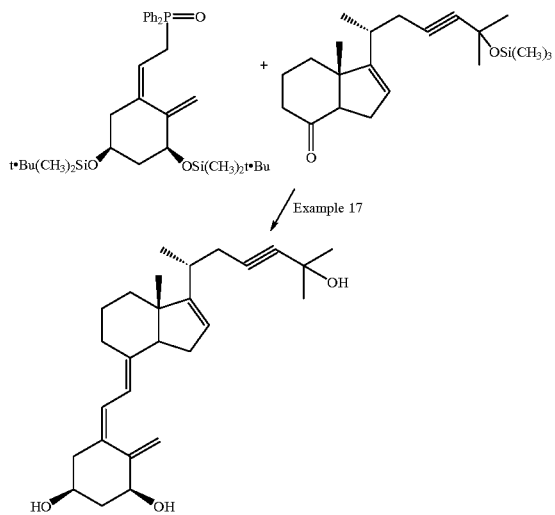

3-epi-1,25-Dihydroxy-16-ene-25-yne-cholecalciferol.

To a stirred, cold (-78° C.) solution of 1.75 g (3.0 mmol) of the reagent [3S-(1Z,3α,5α)]-2-[3,5-bis[[(1,1-dimethyl)-dimethylsilyl]oxy]-2-methylenecyclohex-ylidene]ethyl] diphenylphosphine oxide (Ro 27-5110) in 6.0 mL of anhydrous THF was added 1.9 mL (3.04 mmol) of a 1.6 M solution of n-butyllithium in hexanes. The resultant red solution was stirred at -78° C. for 6 minutes and treated with 520 mg (1.50 mmol) of [3aR-[1(R*), 3aα, 7aβ]]-1-[1,5-dimethyl-5-[(trimethylsilyl)oxy]-3-hexynyl]-3a,5,6,7,7a-hexahydro-7a-methyl-4H-inden-4-one in 3.0 mL of anhydrous THF. The mixture was stirred at -78° C. for 2.5 hours, allowed to warm to 0° C. and quenched with 10 mL of a 1:1 mixture of 2.0 M Rochelle salt solution and 2.0 M solution of KHCO$_3$. After 10 minutes, the mixture was poured into 70 mL of ethyl acetate and 50 mL of a 1:1 mixture of 2.0 M Rochelle salt solution and 2.0 N KHCO$_3$ solution. The organic phase was separated and the aqueous phase was re-extracted with 3×60 mL of ethyl acetate. The combined organic extracts were dried (Na$_2$SO$_4$) and evaporated to give 1.35 of a gum, which was purified by flash chromatography on 50 grams of silica gel (40–65 µm mesh; 3.5 cm diameter column) with 8% ethyl acetate in hexanes as eluent, taking 15-mL fractions. Fractions 4 and 5 were combined and evaporated to give 153 mg of a colorless gum. The latter was dissolved in 3.0 mL of THF, treated with 2.0 mL of a 1.0 M solution of tetra-n-butylammonium fluoride in THF and the solution was stirred at room temperature for 17.0 hours. It was diluted with 6.0 mL of water and 15 mL of ethyl acetate and stirred for 15 minutes. The mixture was poured into 50 mL of ethyl acetate and 50 mL of 10% brine. The organic phase was separated and the aqueous phase was extracted with 3×60 mL of ethyl acetate. The combined organic extracts were washed with 4×100 mL of water, dried (Na$_2$SO$_4$) and evaporated to give 108 mg of a gum, which was chromatographed on 40 grams of flash silica gel (40–65 µm mesh; 3.5 cm diameter column) with ethyl acetate as eluent, taking 15-mL fractions. Fractions 12–18 were combined and evaporated. The residue was dissolved in 10 mL of anhydrous methyl formate and the solution was filtered through a 0.4 µm filter. Evaporation of the filtrate gave 84 mg of the title compound as a colorless foam: [α]S(25,D) -47.8° (MeOH, c=0.41); UV (MeOH) 262 (ε=17,060), 210 (ε=12,094 shoulder), nm; IR (CHCl$_3$) 3603, 3516, 2224 cm$^{-1}$; $^1$H NMR (CDCl$_3$) δ 0.71 (3H, s), 1.12 (3H, d, J=6.8 Hz), 1.48 (6H, s), 1.60–1.80 (5H,m), 2.0 (3H, m), 2.17–2.25 (3H, m), 2.30–2.40 (3H, m), 2.44 (1H, dd, J=13,5), 2.57 (1H, d, J=13 Hz), 2.64 (1H, d, J=6.8 Hz, OH), 2.84 (1H, d, J=12 Hz), 4.07 (1H, br s), 5.01 (1H, s), 5.311 (H, s), 5.37 (1H, s), 6.10 (1H, d, J=11 Hz), 6.43 (1H, d, J=11 Hz); MS (FAB) m/z 410.5 (M$^+$, 80).

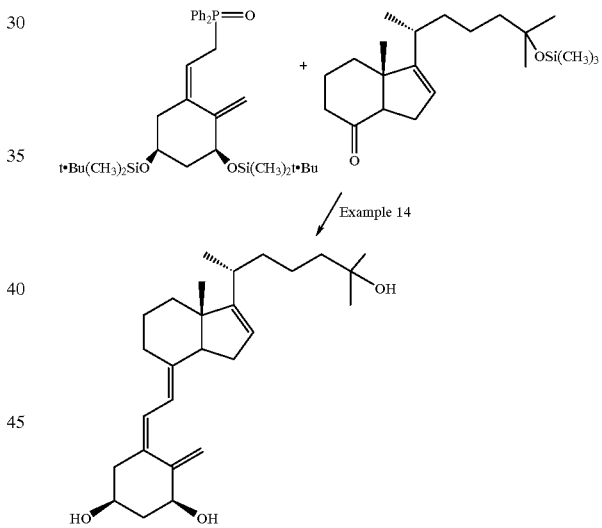

3-epi-1,25-Dihydroxy-16-ene-cholecalciferol. To a stirred, cold (-78° C.) solution of 582.9 mg (1.0 mmol) of the reagent [3 S-(1Z,3α,5α)]-2-[3,5-bis[[(1,1 -dimethylethyl)-dimethylsilyl]oxy]-2-methylenecy-clohexylidene]ethyl] diphenylphosphine oxide (Ro 27-5110) in 5.0 mL of anhydrous THF was added 0.63 mL (1.0 mmol) of a 1.6 M solution of n-butyllithium in hexanes. The resultant deep red solution was stirred at -78° C. for 20 minutes and treated with 175.3 mg (0.5 mmol) of [3aR-[1(R*), 3aα, 7aβ]]-1-[1,5-dimethyl-5-[(trimethylsilyl)oxy]hexyl]-3,3a,5,6,7,7a-hexahydro-7a-methyl-4H-inden-4-one in 2.0 mL of anhydrous THF. The mixture was stirred at -78° C. for 3.0 hours, allowed to warm to room temperature and quenched with 10 mL of a 1:1 mixture of 1.0 M Rochelle salt solution and 1.0 N KHCO$_3$ solution. After 15 minutes, the mixture was poured into 60 mL of ethyl acetate and 40 mL of a 1:1 mixture of 1.0 M Rochelle salt solution and 1.0 N KHCO$_3$ solution. The organic phase was separated and the aqueous phase was re-extracted with 3×50 mL of ethyl acetate. The combined organic extracts were washed with 10% brine, dried (Na$_2$SO$_4$), and evaporated to give 719 mg of a gum, which was purified by flash chromatography on 50 grams of silica gel (40–65 μm mesh; 3.5 cm diameter column) with 5% ethyl acetate in hexanes as eluent, taking 15-mL fractions. Fractions 3–5 were combined and evaporated to give 323 mg of a colorless gum. The latter in 7.0 mL of THF was treated with 3.5 mL (3.5 mmol) of a 1.0 M solution of tetra-n-butylammonium fluoride in THF and the solution was stirred at room temperature for 18 hours. It was diluted with 15 mL of water, stirred for 15 minutes and poured into a mixture of 75 mL of ethyl acetate and 60 mL of 10% brine. The organic phase was separated and the aqueous phase was re-extracted with 3×60 mL of ethyl acetate. The combined organic extracts were washed with 4×75 mL of water, dried (Na$_2$SO$_4$) and evaporated to give 191 mg of a gum, which was purified by flash chromatography on 40 grams of silica gel (40–65 μm mesh; 3.5 cm diameter column) with ethyl acetate as eluent, taking mL fractions. Fractions 10–25 were combined and evaporated. The residue was dissolved in 10 mL of methyl formate, and the solution was filtered through a 0.4 μm filter and evaporated to give 164 mg of the title compound as an amorphous solid: [a]S(25,D) −47.72° (MeOH, c=1.01); UV (MeOH) λmax 263 (ε=17,027), 218 (12,368, shoulder) 209 (16, 082) nm; IR (CHCl$_3$) 3606, 3513 cm$^{-1}$; $^1$H NMR (CDCl$_3$)δ 0.68 (3H, s), 1.02 (6H, d, J=6.8 Hz), 1.19 (6H, s), 1.29–2.5 (H, m), 2.57 (1H, d, J=12.8), 2.84 (1H, d, J=12.8), 4.05 (1H, s), 4.31 (1H, br t), 5.02 (1 H, s), 5.29(1H, s), 5.31 (1H, s), 6.11 (1H, d, J=1 Hz), 6.43 (1H, d, J=1 Hz); MS (EI) m/z 414.3 (M$^+$, 60).

with 10 mL of a 1:1 mixture of 2.0 M Rochelle salt solution and 2.0 N KHCO$_3$ solution. After 25 minutes, the mixture was poured into a 1:1 mixture of 2.0 M Rochelle salt solution and 2 N KHCO$_3$ solution. The organic phase was separated and the aqueous phase was re-extracted with 3×60 mL of ethyl acetate. The combined organic extracts were washed with 50% brine, dried (Na$_2$SO$_4$), and evaporated to give 764 mg of a gum, which was purified by flash chromatography on 50 g of silica gel (40–60 mμ mesh; 3.5 cm diameter column) with 7% ethyl acetate in hexanes as eluent, taking 15-mL fractions. Fractions 5–12 were combined as evaporated to give 321 mg of a colorless gum. The latter was dissolved in 4.0 mL of THF, treated with 4.0 mL (4.0 mmol) of a 1.0 M solution of tetra-n-buthylammonium fluoride in THF, and the solution was stirred at room temperature for 18 hours. It was diluted with 10 mL of water, stirred for 15 minutes, and poured into a mixture of 75 mL of ethyl acetate and 60 mL of 10% brine. The organic phase was separated and the aqueous phase was reextracted with 3×60 mL of ethyl acetate. The combined extracts were washed with 4×100 mL of water, dried (Na$_2$SO$_4$), and evaporated to give 233 mg of a gum, which was purified by flash chromatography on 40 g of silica gel (40–60 mμ; 3.5 cm diameter column) with ethyl acetate as eluent, taking 15-mL fractions. Fractions 8–13 were combined and evaporated and the residue was dissolved in 10 mL of anhydrous methyl formate. The solution was filtered through a 0.4 μm filter and the filtrate was evaporated to give 181 mg of the title compound as a colorless foam: [α]S(25,D) −33.13° (MeOH, c=0.51); UV (MeOH) λ$_{max}$ 263 (ε=17,431), 241 (ε=13,258, shoulder), 217 (ε=13,002, shoulder) 211 (ε=14, 950) nm; IR (CHCl$_3$) 3594, 2261, 2239, 1195 cm$^{-1}$; $^1$H NMR (CDCl$_3$) δ 0.70 (3H,s), 1.14 (3H, d, J=6.8 Hz), 1.50 (1H, m), 1.6–1.85 (4H, m) 2.05 (3H, m), 2.30 (2H, m), 2.40 (5H, m), 2.58 (1H, m), 2.83 (2H, m), 3.73 (1H, s, OH) 4.07 (1H, br s), 4.33(1H, br s), 5.01 (1H, s), 5.30 (1H, s), 5.41 (1H, s), 6.10 (1H, d, J=1 Hz), 6.43 (1H, d, J=11 Hz); MS (EI) m/z 518.4 (M$^+$, 60).

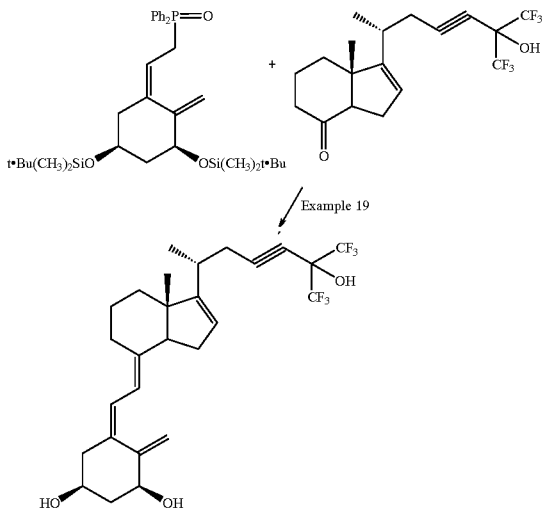

3-epi-1,25-Dihydroxy-16-ene-13-yne-hexafluorocholecalciferol. To a stirred, cold (−78° C.) solution of 582.9 mg (1.0 mmol) of the reagent [3S-(1Z,3α,5α)]-2-[3,5-bis[[(1,1-dimethylethyl)-dimethylsilyl]oxy]-2-methylenecyclohexylidene]ethyl]diphenylphosphine oxide (Ro 27-5110) in 5.0 mL of anhydrous THF was added 0.63 mL of a (1.0 mmol) 1.6 M solution of n-butyllithium in hexanes and the resultant deep red solution was stirred at −78° C. for 17 minutes and treated with 191.17 mg (0.5 mmol) of [3aR-[1(R*), 3aα, 7aβ]]-3a,5,6,7,7a-hexahydro-7a-methyl-1-[6,6,6-trifluoro-5-hydroxy-1-methyl-5-(trifluoromethyl)-3-hexynyl]-4H-inden-4-one in 2.5 mL of anhydrous THF. The mixture was stirred at −78° C. for 3.0 hours, allowed to warm to room temperature and quenched

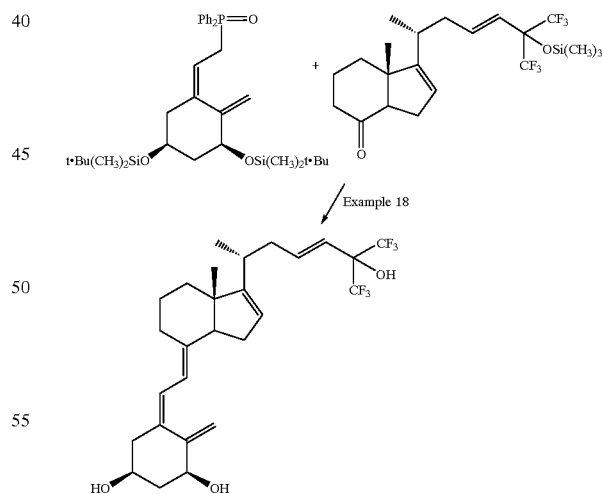

3-epi-1,25-Dihydroxy-16,23E-diene-26,27-hexafluorocholecalciferol. To a stirred, cold (−78° C.) solution of 385.0 mg (0.66 mmol) of the reagent [3S-(1Z,3α,5α)]-2-[3,5-bis[[(1,1-dimethylethyl)-dimethylsilyl]oxy]-2-methylenecyclohexylidene]ethyl]diphenylphosphine oxide (Ro 27-5110) in 4.0 mL of anhydrous THF was added 0.42 mL (0.67 mmol) of a 1.6 M solution of n-butyllithium in hexanes and the resultant deep red solution was stirred at −78° C. for 20 minutes and treated with 128.1 mg (0.33 mmol) of [3aR-[1(R*), 3aα, 7aβ]]-3a,5,6,7,7a-hexahydro-7a-methyl-1-[6,6,6-trifluoro-1-methyl-5-(trifluoro-methyl)-5-[(trimethylsilyl)oxy]-3-hexenyl]-4H-inden-4-one in 2.0 mL of anhyd-rous THF. The mixture was stirred at −78° C. for 3.0 hours, allowed to warm to room temperature and quenched with 5.0 mL of a 1:1 mixture of 1.0 M Rochelle salt solution and 1.0 N KHCO$_3$ solution. After 10 minutes, the mixture was poured into 60 mL of ethyl acetate and 35 mL of a 1:1 mixture of 1.0 M Rochelle salt solution and 1 N KHCO$_3$ solution. The organic phase was separated and the aqueous phase was reextracted with 3×40 mL of ethyl acetate. The combined organic extracts were washed with 150 mL of 50% brine, dried (Na$_2$SO$_4$), and evaporated to give gum, which was purified by flash chromatography on 45 g of silica gel (40–60 mμ mesh; 3.5 cm diameter column) with 20% ethyl acetate in hexanes as eluent, taking 15-mL fractions. Fractions 4–6 were combined as evaporated to give 244 mg of a colorless gum. The latter was dissolved in 3.5 mL of THF, treated with 2.5 mL (2.5 mmol) of a 1.0 M solution of tetra-n-buthylammonium fluoride in THF, and the solution was stirred at room temperature for 17 hours. It was diluted with 5 mL of water, stirred for 15 minutes, and poured into a mixture of 50 mL of ethyl acetate and 40 mL of 10% brine. The organic phase was separated and the aqueous phase was reextracted with 3×40 mL of ethyl acetate. The combined extracts were washed with 4×100 mL of water, dried (Na$_2$SO$_4$), and evaporated to give 176 mg of a gum, which was purified by flash chromatography on 40 g of silica gel (40–60 mμ mesh; 3.5 cm diameter column) with ethyl acetate as eluent, taking 15-mL fractions. Fractions 8–15 were combined and evaporated and the residue was dissolved in 10 mL of anhydrous methyl formate. The solution was filtered through a 0.4 μm filter and the filtrate was evaporated to give 131 mg of the title compound as a colorless solid: [α]S(25,D) −33.4° (MeOH, c=0.53); UV (MeOH) λ$_{max}$ 262 (ε=14,835), 218 (ε=10,960, shoulder), 209 (ε=13,793) nm; IR (CHCl$_3$) 3596, 2261 cm$^{-1}$; $^1$H NMR (CDCl$_3$) δ 0.67 (3H, s), 1.04 (3H, d, J=6.8 Hz), 1.50 (1H, m), 1.6–1.85 (4H, m) 2.05 (3H, m), 2.25 (4H, m), 2.40 (3H, m), 2.55 (1H, m), 2.74 (1H, d, J=6.8 Hz), 2.84 (1H, br d, J=13 Hz), 3.26 (1H, s, OH), 4.06 (1H, br s), 4.33 (1H, br s), 5.01 (1H, s), 5.30(1H, s), 5.32(1H, s), 5.60(1H, d, J=16Hz), 6.10(1H, d, J=11 Hz), 6.16 (1H, dt,J=16, 7.6) 6.43 (1H, d, J=Hz); MS (FAB) m/z 520 (M$^+$, 20).

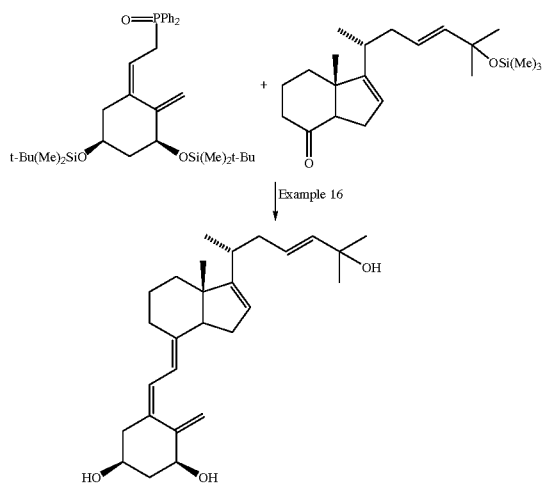

3-epi-1,25-Dihydroxy-16,(E)23-diene-cholecalciferol.

To a stirred, cold (−78° C.) solution of 582.91 mg (1.0 mmol) of the reagent [3S-(1Z,3α,5α)]-2-[3,5-bis[[(1,1-dimethylethyl)-dimethylsilyl]oxy]-2-methylenecyclo-hexylidene]ethyl]diphenylphosphine oxide (Ro 27-5110) in 6.0 mL of anhydrous THF was added 0.63 mL (1.00 mmol) of a 1.6 M solution of n-butyllithium in hexanes and the resultant deep red solution was stirred at −78° C. for 20 minutes and treated with 200 mg (0.57 mmol) of 1-[1,5-dimethyl-5-[(trimethylsilyl)oxy]-3-(E)hexenyl]-3,3a,5,6,7,7a-hexahydro-7a-methyl-[3aR-[1(R*), 3aα, 7aβ]]-4H-inden-4-one in 2.0 mL of anhydrous THF. The mixture was stirred at −78° C. for 3.0 hours, allowed to warm to room temperature and quenched with 10.0 mL of a 1:1 mixture of 1.0 M Rochelle salt solution and 1.0 N KHCO$_3$ solution. After 10 minutes, the mixture was poured into 70 mL of ethyl acetate and 45 mL of a 1:1 mixture of 1.0 M Rochelle salt solution and 1 N KHCO$_3$ solution. The organic phase was separated and the aqueous phase was reextracted with 3×60 mL of ethyl acetate, washed with 150 mL of 10% brine, dried (Na$_2$SO$_4$) and evaporated to give a colorless gum, which was purified by flash chromatography on 50 g of silica gel (40–60 mμ mesh; 3.5 cm diameter column) with 7.5% ethyl acetate in hexanes as eluent, taking 15-mL fractions. Fractions 5–10 were combined as evaporated to give 382 mg of a colorless gum. The latter was dissolved in 6.0 mL of THF, treated with 5.0 mL (5.0 mmol) of a 1.0 M solution of tetra-n-butylammonium fluoride in THF, and the solution was stirred at room temperature for 17 hours. It was diluted with 10 mL of water and poured into a mixture of 75 mL of ethyl acetate and 50 mL of 10% brine. The organic phase was separated and the aqueous phase was reextracted with 3×75 mL of ethyl acetate. The combined extracts were washed with 4×150 mL of water, dried (Na$_2$SO$_4$), and evaporated to give 280 mg of a semi-solid, which was purified by flash chromatography on 50 g of silica gel (40–60 μm mesh; 3.5 cm diameter column) with 1.0% 2-propanol in ethyl acetate as eluent, taking 15-mL fractions. Fractions 17–29 were combined and evaporated to give 204 mg of a solid, which was dissolved in 10 mL of anhydrous methyl formate. The solution was filtered through a 0.45 μm filter and the filtrate was concentrated to ca. 5.0 mL and then diluted with 0.5 mL of hexane. The solution was left at 0° C. overnight and the crystals were collected by filtration and dried under high vacuum to give 147 mg of the title compound, mp 106–109° C.; [α]S(25,D) −64.24 (MeOH, c=0.33); UV (MeOH) λ$_{max}$ 263 (ε=18,445), 220 (shl, ε=12,524), 211 (shl, ε=17,145) nm; IR (CHCl$_3$) 3609 cm$^{-1}$; $^1$H NMR (CDCl$_3$) δ 0.67 (3H, s), 1.01 (3H, d, J=6.8 Hz), 1.29 (6H, s), 1.33 (1H, s, OH), 1.52 (1H, m), 1.65–1.90 (4H, m), 2.05–2.30 (8H, m), 2.37 (1H, m), 2.45 (1H, m), 2.64 (1H, br d, OH), 2.83 (1H, br d), 4.06 (1H, br s), 4.31 (1H, br s), 5.02 (1H, s), 5.31 (1H, s), 5.59 (2H, m), 6.10 (1H, d, J=11 Hz), 6.43 (1H, d, J=11 Hz); MS (electrospray) m/z 412 (M$^+$).

We claim:

1.

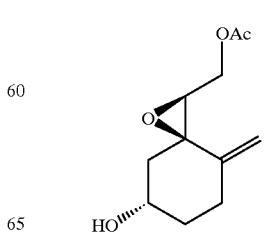

V

2.
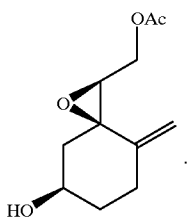
3.
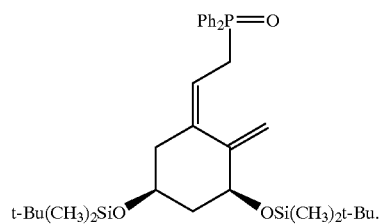
VII
II
* * * * *